(12) United States Patent
Blacklock et al.

(10) Patent No.: US 8,545,561 B2
(45) Date of Patent: Oct. 1, 2013

(54) ORTHOPAEDIC MEDICAL DEVICE

(75) Inventors: Terence Blacklock, Lancashire (GB); Frank Bleistein, Alzenau (DE)

(73) Assignee: Taurus GmbH & Co. KG, Alzenau (DE)

( * ) Notice: Subject to any disclaimer, the term of this patent is extended or adjusted under 35 U.S.C. 154(b) by 1822 days.

(21) Appl. No.: 11/461,873

(22) Filed: Aug. 2, 2006

(65) Prior Publication Data
US 2007/0032875 A1 Feb. 8, 2007

(30) Foreign Application Priority Data

Aug. 4, 2005 (GB) .................................. 0516034.6

(51) Int. Cl.
*A61F 2/44* (2006.01)
(52) U.S. Cl.
USPC ..................................... 623/17.11; 623/17.15
(58) Field of Classification Search
USPC .......................................... 623/17.15–17.16
See application file for complete search history.

(56) References Cited

U.S. PATENT DOCUMENTS

| | | | |
|---|---|---|---|
| 4,759,766 A * | 7/1988 | Buettner-Janz et al. ... | 623/17.15 |
| 4,759,769 A | 7/1988 | Hedman et al. | |
| 5,401,269 A | 3/1995 | Buttner-Janz et al. | |
| 5,676,701 A * | 10/1997 | Yuan et al. ................. | 623/17.15 |
| 6,626,943 B2 * | 9/2003 | Eberlein et al. ............ | 623/17.15 |
| 6,793,678 B2 * | 9/2004 | Hawkins ..................... | 623/17.15 |
| 6,989,032 B2 * | 1/2006 | Errico et al. ................ | 623/17.14 |
| 6,994,727 B2 * | 2/2006 | Khandkar et al. .......... | 623/17.15 |
| 7,025,787 B2 * | 4/2006 | Bryan et al. ................ | 623/17.16 |
| 7,393,361 B2 * | 7/2008 | Zubok et al. ............... | 623/17.15 |
| 2003/0204271 A1 | 10/2003 | Ferree | |
| 2004/0034426 A1 * | 2/2004 | Errico et al. ............... | 623/17.13 |
| 2004/0117021 A1 | 6/2004 | Biedermann et al. | |
| 2004/0143332 A1 * | 7/2004 | Krueger et al. ............ | 623/17.14 |
| 2005/0154468 A1 * | 7/2005 | Rivin .......................... | 623/17.16 |
| 2005/0159818 A1 * | 7/2005 | Blain .......................... | 623/17.15 |

FOREIGN PATENT DOCUMENTS

| | | |
|---|---|---|
| CA | 2510244 | 7/2004 |
| DE | 4213771 | 9/1993 |
| WO | 0053127 | 9/2000 |
| WO | 0115638 | 3/2001 |

OTHER PUBLICATIONS

International Search Report with Observations dated Jan. 26, 2007 received in corresponding International Patent Application No. PCT/EP2006/007658 (13 pages).

* cited by examiner

*Primary Examiner* — Nicholas Woodall
(74) *Attorney, Agent, or Firm* — Grossman Tucker Perreault & Pfleger, PLLC (57) ABSTRACT

An artificial disc having a pair of opposing plates (100) for seating against opposing vertebral bone surfaces separated by an inner stress distributor and spacer device (300) called in this specification a supporting element, functioning as both a spacer and structural support. Various plate geometries are disclosed including ones with flat outer faces and ones with convex outer faces to conform to the adjacent vertebral mating surface geometry. Inner surfaces are described as comprising two sloping substantially flat or curved surfaces meeting at an ridgeline with a radius. Various inner device embodiments are disclosed including circular ones and non-circular ones, plate flat ones, ones with a raised rim or circular recess, ones with raised hubs and ones with an elastomeric planar core to perform a shock-absorbing function, ones with central bore and ones with no central bore. Inner spacers comprising various combinations of these features are disclosed. The inner spacer/support devices are dispersed between the plates, through various disclosed couplings, so that the plates compress, rotate and angulate freely relative to one another, enabling the artificial disc to mimic a healthy natural intervertebral disc.

21 Claims, 10 Drawing Sheets

ORTHOPAEDIC MEDICAL DEVICE

This invention relates generally to a spinal implant assembly for implantation in to the intervertebral space between adjacent vertebra simultaneously to restore proper anatomical motion and provide stabilisation and more specifically to such a device that utilises plates with angled planes and a force spreading support element.

The human spine is a complex assembly of substantially cylindrically shaped bones connected by disc shaped cartilage based elements in a curved or more or less 'S' shaped arrangement and is divided into anatomical regions with seven cervical vertebrae at the top (from under the base of the skull), twelve thoracic vertebrae in the middle section and five lumbar vertebrae towards the base of the spine.

In some patients the cartilage discs become damaged or diseased, often requiring surgical intervention to make repairs to completely remove the affected disc. Surgical procedures may include the introduction of devices that promote fusion between adjacent vertebrae, so called spinal fusion. This procedure removes the ability of the affected vertebrae to articulate relatively to one another and some degree of spinal flexibility is lost as a result. By contrast, there is increasing levels of interest in alternative technologies that allow the affected disc to be replaced with an artificial joint, restoring mobility between the adjacent vertebrae. However, these systems rely on the sliding of a moveable element over the surface of a second or third element. Such sliding creates the increased possibility of wear debris generation, limiting the lifetime of the device.

According to the present invention, there is provided an intervertebral body spacer device for motion preservation, comprising first and second plates with inner and outer surfaces, said plates being disposed in a spaced apart relationship with the inner surface of the first plate facing the inner surface of the second plate, both inner surfaces being separated by a contacting element.

Briefly, the device is an artificial intervertebral disc, comprising a pair of support members (such as a pair of spaced apart plates), each with an exterior surface. The plates are arranged substantially parallel to one another, but may be tilted relative to one another in vivo, taking the natural lordotic conformation set by the adjacent vertebral bodies. The outer surfaces of the plates face outwards and sit in abutment to the bony surfaces of the adjacent vertebras in a columnar configuration. The artificial disc plates are to mate with the adjacent vertebras so as to allow normal spine biomechanical motion whilst achieving attachment to the adjacent vertebral bodies by physical means. Natural motion is achieved through the interaction of the inner surfaces of the plates which are shaped to predispose an articulating motion mating against an inner contact element (such as a disc) which is both a spacer and means of reducing the contact stresses between the two inner faces. Securing of the outer surfaces of a plate and the mating vertebral element bony surface is achieved through a contact element. Examples of contact elements include: machined or moulded surface texture, teeth, spikes, the bonding onto the surface or hot pressing or moulding into the surface of metallic mesh or trabecular metal (for example as open cell tantalum metal) or coating with titanium or alloys of titanium or other biocompatible metal in thin layers or as beads, tricalcium phosphates, Hydroxy appatites or other known in the art means of attachment between biomaterials and bone to achieve osteo-conduction or osseointegration, including the use of bone morphogenic proteins (BMPs) and artificial or natural bone regenerating compounds. The inner faces of at least one or each plate are shaped such as to form two planar or non-planar sloping surfaces that meet at a linear ridgeline, preferably in a direction along the longest extent of one plate and across the width of the opposite plate, such that the linear apices are disposed at an angle, preferably substantially at right angles, to one another, facing one another. Each ridgeline may be arranged to be positioned substantially along the central axis of each plate in the predetermined direction, but it is to be understood that some offset may be designed into the positioning of each ridgeline. Likewise, the surfaces may be plane or curved or in a convex format and the ridgeline at which the two surfaces meet may have a radius. The ridgelines of the two plates being separated by a contacting element are arranged facing each other. Especially, the ridgeline may be linear and/or may be arranged in a plane in which preferably a main axis of the plate is arranged. Especially, the device may comprise just one first and one second plate. Furthermore, the device may comprise just one contacting element separating two adjacent plates having ridgelines, however, the just one contacting element may have a multi-layer construction. In certain cases, the device may comprise more than one contacting element each being arranged between a first and a second plate having a ridgeline, respectively, so that the device may e.g. be a sandwich construction comprising more than three, e.g. five or more, members of the group consisting of plates and contacting elements. Especially in some cases the contacting element may be an integrally moulded element or a one-piece element.

Preferred embodiments are disclosed in the subclaims.

In one embodiment the plates are curved with an inner radius to facilitate installation translaminarly. The inner surfaces of the plates may have a circular or oval or other shaped recess to accommodate part of the thickness of the supporting component disposed between the plates.

The inner surface of one or both plates may be non-circular curved, while the curvature of the ridgeline area of the plate may be higher than the curvatures of the adjacent sloping portions of the end plates, for instance ≥3, 5 or 10 times of it.

In case the inner surface of one or both plates are curved, the curvature may be within a plane arranged perpendicularly to the ridgeline and/or within a plane being parallel to the ridgeline but being arranged at least substantially perpendicularly to the "horizontal" main plane of the plate.

The contacting area of the contacting element which may be in contact with the ridgeline of at least one or both plates in the assembled state of the device may have a curvature so that the magnitude of degree of curvature is lower that that of the ridgeline. This may be the case for any tilted arrangement of the at least one or both plates with respect to the contacting element.

Especially, the ridgeline portion of one or both of the plates may at least substantially be fixed in its spatial relationship to the contacting element, so that by tilting or rolling the one or both plates around the ridgeline the ridgeline is at least substantially not shifted or moved with its contacting area with respect to the contacting element. This may be the case, even if the at least one plate is rotatable around its main axis in relation to the contacting element. During the rolling motion of the plate, the ridgeline may become out of contact with the contacting element, so that a portion of the inner surface of the plate being arranged just beside the ridgeline will become in contact with the contacting element, especially at the maximum degree of the rolling motion. This especially may be the case, if the ridgeline is curved instead of being designed as a sharp edge. Especially, during the tilting motion the axis around which the plate is tilted is moved with respect to the contacting element and/or the other plate. A gap between the contacting surfaces of the plate and the contacting element which are in engagement with each other at a certain arrangement the plate the element may be closed or opened in course of the tilting motion.

The sloping surfaces of the inner surface of at least one or both plates which are arranged on opposite sides of the ridgeline of a given plate may be different to each other, especially may have different curvatures or different sloping angles in case the surfaces are flat planes. This especially may be the case for the surfaces of a plate being arranged on the front side and the back side of the person, when the device is implanted.

The supporting component disposed between the plates provides a means of spreading the compressive load as it passes through the plate arrangement, avoiding a substantially point to point contact between the two opposing plate inner faces that would occur if they mated directly. Especially, the contact between one or both of the plates and the contacting element may be substantially a line-like contact, especially a linear one. The lateral extension of the contact area may be substantially lower than the lateral extension of the sloping areas of the plates.

In one embodiment of the invention, the central supporting element (contacting element) has a raised part that locates within a hole or slot cut into the adjacent plates disposed above and below the supporting element. The raised part may be a locatable cylindrical or elongated hub. The upper slot and lower slots may be arranged with their longest axis perpendicular to one another so as to enable the disc and plates to move laterally with respect to one another as may be required to conform to spine biomechanics. The raised part on the supporting element may be elongated such that when it is located within the slots on the plate inner surfaces, the raised part prevents rotation of the supporting element relative to the adjacent plates whilst still allowing the plates to compress and move in a manner that mimics normal spinal motion.

The raised part of the contacting element may be arranged in the slot with play in the longitudinal direction of the slot and with no or substantially no play in a direction transverse to it, so that the raised part ca be is shifted predominantly or exclusively in the longitudinal direction of the slot.

The supporting element may be made from one hard/stiff material or it may comprise a number of materials (hard and soft) in a sandwich configuration so as to impart a shock absorbing quality to the supporting element loaded in compression.

The supporting element may be fixed or not fixed in assembly with the mating plates. Fixing may be achieved with any suitable means. Fixing may be achieved with mechanical fastening, especially with form-fit means. Fixing may be achieved with wire or thread passing through the plates and a central bore through the supporting element. Thread may be dissolvable stitching material.

At least one of the inner surfaces of opposing plates may contain a locating recess preferably substantially in the centre of the plate and preferably with a depth about half the thickness of the contacting element, or lower or higher, and into which the contacting element movably locates.

The upper and lower plates may be connected by means of a flexible gasket adhesively bonded between the plates. The gasket may have a space in the middle to locate the central supporting element. The edges of the gasket may be shaped to conform to the topography formed between the two facing inner surfaces of the plates and such that it allows full bending movement as required to replicate normal spine motion.

The contacting element may be provided with raised locatable parts which are locatable in slots being machined in the plates. The raised locatable parts may be integrally moulded with the contacting element or may be separated elements which do establish a functional unity, e.g by a separate bolt member which may be fastened to the engaging element, preferably in a non-detachable fashion.

The upper and lower plates may be fastened with the contacting element by mechanical means being designed as a bolt which is arranged in a through-hole of the contacting element. The bolt may be provided with opposite head portions which are fastened at the first and the second plates. The first and second head portions of the bolt may be arranged in corresponding recesses of the first and second plates. To fasten the head portions of the bolt, the recesses of the first and second plates may be provided with undercuts which are cooperating with the head portions of the bolt to avoid a separation of the device. Especially, the bolt may be a two-part member, both parts of which may be fastened or fixed with each other by form-fit means and/or by friction means. Especially, the fastening portions of the first and second part of the bolt may be designed as a sleeve member and as a pin member which can be introduced into the sleeve member in fastening engagement to provide a press-fit and/or frictional fastening action. In general, the bolt may be attached to the contacting element so that the bolt cannot be shifted in its longitudinal direction relative to the contacting element. Especially, the first and second part of the bolt may be provided with contacting areas which engages the upper and lower faces of the contacting element which are facing the upper and lower plates. The contacting area of the bolt parts may be designed as circumferential steps or flanges.

The fastening portions of the mechanical means, especially the head portions of the bolt, may be fastened at the upper and lower plates in a manner enabling a slight displacement of the plates in the longitudinal direction of the mechanical means, so that the upper and lower plates may be tilted around the ridgeline relative to each other or to the contacting element even in case the elements mentioned above are not deformed during the tilting motion.

The fastening means for fastening the contacting element to the plates, especially in case they are designed as mechanical means, may be provided with end portions which are arranged within a recess of the corresponding upper or lower plate. The recesses of the plates may have a port being opened towards the contacting element and may have a further port facing away from the contacting element, especially being arranged opposite to the first port. The ports facing away from the contacting element may be closed by closure means which hinder or prevent bone material to grow into the recesses of the upper and lower plates. The closure means may be designed as closure plates. The closure means may be fastened at the corresponding upper and lower plates by any suitable means, especially by form-fit means or snap means, by threaded portions provided at the closure means and the plates or by welding, especially in case the closure means and/or the area of the plates being adjacent to the closure means are made of plastic material. Especially, the closure means may be fastened to the plates in non-detachable manner, including non-detachable in their closure position.

The first and second plate may be provided with teeth. The teeth may be arranged irregularly and/or may have different heights to enhance the bone material to be fastened at the outer surfaces of the first and second plate.

The invention includes an intervertebral body spacer device for motion preservation including two plates with inner surfaces and outer surfaces, the inner surfaces of each plate comprising two smooth sloping faces that meet at a ridgeline and separated by a contacting element in the form of a disc retained in situ by means of a hub located within oriented slots provided or cut into the plates, such that the plates can move relative to one another and/or to the contacting element by means of a rolling action, especially in a relationship similar to normal spinal biomechanics. The ridgelines on the two opposing faces may be disposed at an angle relative to one another, preferably positioned at 45° to 135° or 45° to 120° to one another, e.g. at 60° to 120° degrees or at 45° to 90° degree, most preferably substantially at 90°. In some specific cases the angle may be lower than 45° or higher than 135°.

The intervertebral body spacer device for motion preservation according to the present invention may be made from biocompatible metals, plastics, polymer compounds, polymer composites or ceramics in any combination, including biocompatible carbon fibre reinforced polymers.

For a better understanding of the invention and to show how the same may be carried into effect, reference will now be made, by way of example, to the accompanying drawings, in which:

FIGS. 1.1 and 1.2 are plan views of respectively the inner surfaces and outer surfaces of one plate of an intervertebral body spacer device for motion preservation. FIG. 1.1 shows a central slot in the direction parallel to the ridge line formed between the sloping inner surfaces.

FIG. 1.3 is a side elevation view of the plate showing the recess on the inner surface and tooth-like prominences on the outer surface.

FIG. 1.4 is a front elevation view showing the sloped inner surfaces meeting at an ridgeline that runs along the direction from front to back of the part shown in plan view in FIG. 1.1.

FIG. 1.5 is a sectional view through section A-A of FIG. 1.2 showing the recess on the inner surface and tooth-like prominences on the outer surface.

FIG. 1.6 is a side elevation view of an alternative design, with a convex outer face.

FIGS. 2.1 and 2.2 are plan views of respectively the inner surfaces and outer surfaces of the second plate. FIG. 2.1 shows a central slot in the direction parallel to the ridge line formed between the sloping inner surfaces.

FIG. 2.3 is a sectional view through section A-A of FIG. 2.2 showing the recess on the inner surface and tooth-like prominences on the outer surface.

FIG. 2.4 is a front elevation view of the plate showing the recess on the inner surface and tooth-like prominences on the outer surface.

FIG. 2.5 is a side elevation view showing the sloped inner surfaces meeting at a ridgeline that runs along the direction from left to right across the part shown in plan view in FIG. 2.1.

FIG. 3.1 is a side elevation view of the central support element showing the raised hub.

FIG. 3.2 is a side elevation view of the central support element with raised hub and central bore.

FIG. 3.3 is a side elevation view of the central support element with a recess providing a raised rim.

FIG. 3.4 is a side elevation view of the central support element with a raised hub and raised rim.

FIG. 3.5 is a side elevation view of the central support element with a raised hub in a sandwich configuration with softer elastic material between harder outer layers.

FIG. 3.6 is a side elevation view of the central support element in its simplest form with a hole through the middle.

FIG. 3.7 is a plan view of a support element with a shape similar to but smaller than the adjacent plates. The support element comprises two raised parts, one on top of and one below the support element, each shaped similarly to the locatable slots in the adjacent plates.

FIG. 3.8 is a plan view of a support element with a shape similar to but smaller than the adjacent plates. The support element comprises two raised parts, one on top of and one below the support element, each circular in section and locatable within the slots within the two adjacent plates.

FIG. 3.9 is a plan view of a support element with a circular shape. The support element comprises two raised parts, one on top of and one below the support element, each shaped similarly to the locatable slots in the adjacent plates.

FIG. 3.10 is a plan view of a support element with a circular shape. The support element comprises two raised parts, one on top of and one below the support element, each circular in section and locatable within the slots within the two adjacent plates.

FIG. 4.1 Shows a plan view of the inner face of one plate comprising a shaped channel that can interlock with a suitably designed raised rim of the central support element.

FIG. 4.2 is a front elevation view showing the channel and sloped inner surfaces meeting at a ridge.

FIG. 4.3 is a plan view of the inner surface of the opposite plate with channel and ridge line.

FIG. 4.4 is a side elevation view showing the channel and sloped surfaces meeting at a ridgeline.

FIG. 5.1 is a plan view of the inner surfaces of a plate with ridgeline and slot.

FIG. 5.2 is a front elevation view showing the two sloped faces meeting at the ridgeline.

FIG. 5.3 is a plan view of the inner surface of the second plate with ridgeline set at right angles to the first ridgeline of the first plate and slot running parallel to said ridgeline.

FIG. 5.4 is a side elevation view showing the two sloped surfaces meeting at a ridgeline.

FIG. 6.1 is an assembly drawing in sectional view showing the configuration of the three parts relative to one another with upper plate, supporting central element and lower plate.

FIGS. 6.2 and 6.3 illustrate the motion of the top plate relative to the lower plate in lateral flexion.

FIG. 6.4 shows the plates and central support in their neutral position.

FIGS. 6.5 and 6.6 illustrate the motion of the top plate relative to the bottom plate in flexion and extension.

FIG. 6.7 is an assembly illustration with a circular central support element.

FIG. 6.8 is an assembly illustration with a non-circular central support element.

FIG. 7.1 shows an elastomeric gasket and one of the two plates onto which the gasket is to be adhesively bonded in one embodiment of the invention such that the gasket is sandwiched between the two inner surfaces of the end plates. The gasket is a means of fixing the two plates together with the central supporting element located in position between the two plates.

FIG. 7.2 is a side elevation view of one elastomeric gasket embodiment with a channel along the periphery to facilitate easier angulating motion between the two plates. The gasket is drawn with the upper and lower outer surfaces in flat format, but these surfaces may be contoured to fit the sloping sides of the mating inner surfaces of the plates as shown in FIG. 7.2a.

FIG. 7.3 is the simplest format for the elastomeric gasket; with flat upper and lower surface profiles and no slot or channel around the edge on the perimeter.

FIG. 7.4 is one example of an assembly in side elevation view.

FIG. 8.1 is a sectional view of a further embodiment showing the inner supporting element located between the two plates with protuberances from the supporting element located within slots or holes moulded or machined into the plate inner surfaces of the plates and a mechanical means of attaching the component parts of the assembly together. Said mechanical means in this example is a number of sewing threads passing through the central bore through the supporting element.

FIG. 8.2 is an exploded view illustrating the pathway of one such thread in a simplified version of the assembly. A number of passes of thread is proposed, much like sewing a button onto a fabric garment.

FIG. 11 shows different views of a device according to FIG. 9, wherein the first and second plates are tilted against each other.

Referring now to FIGS. 1.1 to 1.5 and FIGS. 2.1 to 2.5. FIG. 1.1 is a plan view of the inner surface of one end plate 100, illustrating a machined slot 120 and recess 110. The recess may be circular, oval or complex in shape and may vary in depth according to the design. The plate is curved to conform to the anatomical shape of the disc space between vertebrae. A curved edge 115 is provided in this embodiment of the device as a means of aiding device installation during surgery from a posterial or translaminar approach by facilitating a rotational motion in the plane of the plate around the bony protuberances on the vertebra. FIG. 1.2 is a plan view of the outer surface of the end plate. In this example, the outer surface has pyramidal shaped teeth like structure 130 moulded or machined into the surface for the purpose of helping retain the plate in position in vivo by increasing the frictional component of the interaction between the plate outer surface and the mating surface of the adjacent vertabra. Optional tooth free regions 150 are provided in this embodiment for bony on-growth in the form of short pillars that will extend from the bony surface of the vertebral body onto the outer surface of the plate. Bone connection with the plate may be enhanced by known methods in the art, such as coating the outer surface of the plate with a thin layer of titanium by physical vapour deposition or sputter coating, or with tri-calcium phosphate layers, or hydroxyl appatite layers, or by changing the surface chemistry with the addition of BMPs which are protein substances that are active in the promotion of bone regeneration. An alternative to tooth-like protuberances may be to mould onto or into the surface a material such as tribecular metal (tantalum open cell material developed for the purposes of achieving bony ingrowth) or stainless steel mesh. FIG. 1.3 is a side elevation view illustrating the recess 110 in the inner surface and teeth-like structures 130 on the outer surface of the plate. FIG. 1.4 is a front elevation view and shows the sloping inner surfaces 140 in this embodiment of the device. These sloping surfaces and the central load supporting element that will be described in detail later are at the nub of this invention. The sloping surfaces on this plate's inner surface meet at a ridgeline and this runs along one direction only, across the narrow 'front to back' direction of the plate and this is parallel to the long axis of the slot 120 previously described in FIG. 1.1. The ridgeline 112 is shown as a dark heavy line in FIG. 1.1. The load supporting element, described later, sits at and is supported by the inner surfaces that meet at the ridgeline. The design of this embodiment allows the supporting element to rock in a 'seesaw' fashion at this ridgeline. FIG. 1.5 is a sectional view along the direction A-A of FIG. 1.2 and illustrates the recess 110 in the inner surface. Note that the base of the recessed region also has sloping sides as for the main inner surfaces of the device. It is to be understood that the sloped surfaces may have flat faces as in this embodiment, or they may have some degree of curvature such that the rocking motion describes more of an arc. Also, it is to be understood that the ridgeline may be sharp or rounded. FIG. 1.6 is a further embodiment in which the outer surface is not flat, with tooth-like structures, but is curved in a convex manner so as to fit into the anatomical shape of the end face of a vertebral body. The outer face 150 is shown smooth in FIG. 1.6, but this may also be configured to achieve bony connection with the vertebral body as earlier described. It is to be understood at all inner surfaces that mate with the supporting element are to be smooth and/or polished as known in the art for articulating joints such as the hip ball and socket joint, or knee joint or shoulder joint.

FIG. 2.1 is a plan view of the second plate of this embodiment, with recess 210 and slot 220. In this embodiment, the ridgeline 212 runs across the device 'left to right', substantially 90 degrees to that of the first plate earlier described. FIG. 2.2 is a plan view of the outer surface of the device with tooth-like pyramidal features 230 and plane regions 220 earlier described in relation to FIG. 1.2. FIG. 2.3 is a sectional view through A-A of FIG. 2.2 illustrating the recess, slot and tooth-like structures. FIG. 2.4 is a front elevation view and FIG. 2.5 a side elevation view with sloping inner surfaces 240 and tooth-like structures on the outer surface 230. The sloped surfaces may have flat faces as in this embodiment, or they may have some degree of curvature. Especially, the sloped surfaces of both end plates may be flat or may be curved or the surfaces of one end plate may be flat and those of the other one may be curved.

Figure 310:
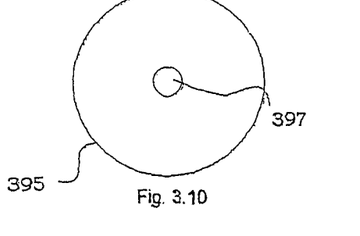

The load supporting element will be described with reference to FIGS. 3.1 to 3.10, which show examples of this component. FIGS. 3.1 to 3.6 are all side elevation views of the supporting element. FIGS. 3.7 to 3.10 are plan views. It is to be understood that the surfaces are to be very smooth/polished. FIG. 3.1 is a planar section with raised central region 305 for location within the slots previously described in connection with FIGS. 1.1 and 2.1. FIG. 3.2 is the same as 3.1, but with a hole 320 through the raised part 315. FIG. 3.3 illustrates a further embodiment with a raised rim 330 and FIG. 3.4 is the same with a raised rim 340 and a raised central part 345. FIG. 3.5 shows a multi-component device with outer parts 350 and 355 and inner part 360. It is intended that the inner part 360 is an elastomeric material such as silicone and that this provides a means of absorbing shock loading in compression when the device is located between the two plates in vivo, what also might be realized with respect to any other embodiment of this invention. FIG. 3.6 is the simplest format for the supporting element, which is a simple washer 365. The plan form shape of the supporting element may be simple round or more complex and the raised parts may be circular or elongated also with respect to any other embodiment of the invention. FIGS. 3.7 to 3.10 illustrate some examples, although it is to be understood that these do not represent all of the possible embodiments of the device. FIG. 3.7 shows one possible outline plan form 375 with plane region 370 and raised elongated parts 377 that are provided on the upper and lower surfaces in a direction offset by substantially 90 degrees and in line with the respective slots on the adjacent plates. FIG. 3.8 illustrates an alternative arrangement for the supporting element 380, but with a circular raised part 387. FIG. 3.9 shows a circular 390 embodiment of the device, with elongated raised parts 393 rotationally offset by approximately 90 degrees. FIG. 310 illustrates the simplest form with circular geometry 395 and circular raised parts 397 for locating into the slots previously described.

The supporting elements described in FIGS. 3.3 and 3.4 require a different configuration on the inner surfaces of the plates than do the remaining embodiments. FIGS. 4.1 to 4.4 illustrate the necessary ring shaped groove provided into the inner surfaces of the plates. This groove may describe a circle or oval or complex shape that matches the perimeter of the supporting element. FIG. 4.1 is a plan view of one of the plates showing the ridgeline as described before and the recessed groove 410 intended to take in mateable union the raised perimeter of the supporting element. FIG. 4.2 is a front elevation view showing the groove in relation to the sloped surfaces. FIG. 4.3 is a plan view of the second plate 420 with groove 430 in relation to the dark ridgeline. FIG. 4.4 is a side elevation view showing the groove 430 in relation to the sloping surfaces.

One of the simplest plate geometries is illustrated in FIGS. 5.1 to 5.4, which illustrate sloping sides 510 and 530, with their ridgeline directions offset by approximately 90 degrees and slots.

It is to be understood that the direction of the ridgelines in any of the preceding embodiments may be disposed in any 360 degree direction around a centre. It is, however, important that the ridgeline direction of the corresponding plate is offset, by more than 45 degrees and more preferably by about 90 degrees to that of the first plate.

FIGS. 6.1 to 6.6 illustrate the relative movement of the plates in assembly with the supporting element located between them. Two plates, as described in FIGS. 5.1 to 5.4 and a circular supporting element with raised central part, as described in FIGS. 3.1 and 3.10, will be used by way of example. FIG. 6.1 shows the upper plate 610 and lower plate 630 in assembly with the central supporting element 620. Load from the human body passing through the vertebral column is applied in a compressive sense to the assembly in vivo. FIGS. 6.2 and 6.3 show how the plates move relatively to one another in a rocking motion in lateral flexion and FIGS. 6.5 and 6.6 illustrate the motion in flexion and extension. In FIGS. 6.7 and 6.8 are isometric drawings showing the relative positioning of the component parts.

Figures 7, 72:
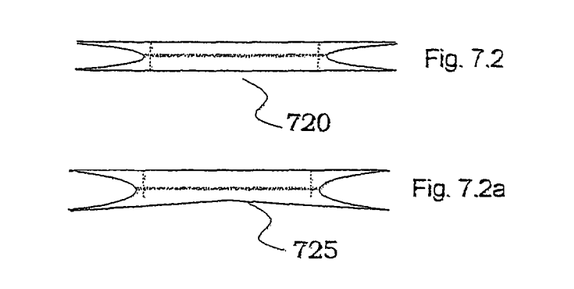

FIG. 7.1 shows an alternative embodiment in which an elastomeric flexible component 700 in the form of a gasket, with a central space to receive the supporting element, is positioned between the plates. The gasket may be manufactured as a separate component and adhesively bonded to join with the two adjacent plates, or it may be cast in situ from pourable or injectable liquid elastic polymer such as silicone rubber. FIG. 7.2 is a front elevation view which illustrates an optional groove 720 around the perimeter of the elastomeric gasket on the edge face and into the body of the gasket, allowing for easier mobility in all directions of motion. The gasket may be shaped or contoured to conform to the shape of the space formed between the plates (FIG. 7.2a). 725 illustrates a contoured surface to fit against the sloped inner surface of the adjacent plate. FIG. 7.3 is a front elevation view of a simpler embodiment with no groove around the edge of the perimeter. FIG. 7.4 is a front elevation view illustrating the assembly configuration comprising an upper plate 740, a lower plate 750, an elastomeric adhesively bonded gasket 746 and central supporting element 770 shown as a dotted-line to illustrate that the supporting element is located within the inner space of the gasket. The gasket serves to join the upper and lower plates together and to keep the supporting element in its correct position while providing full anatomical mobility.

Figure 81:
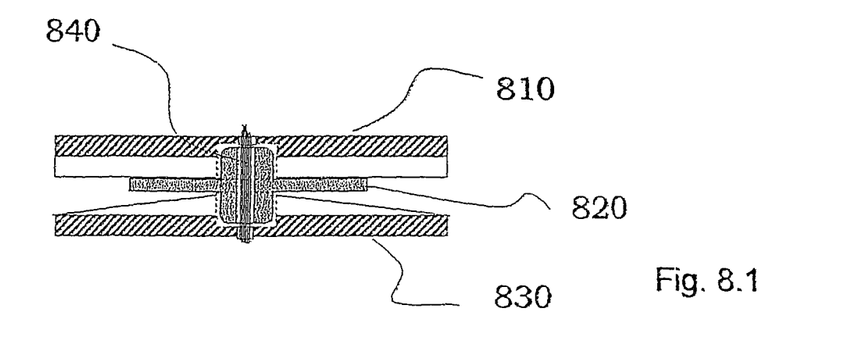
Figure 82:
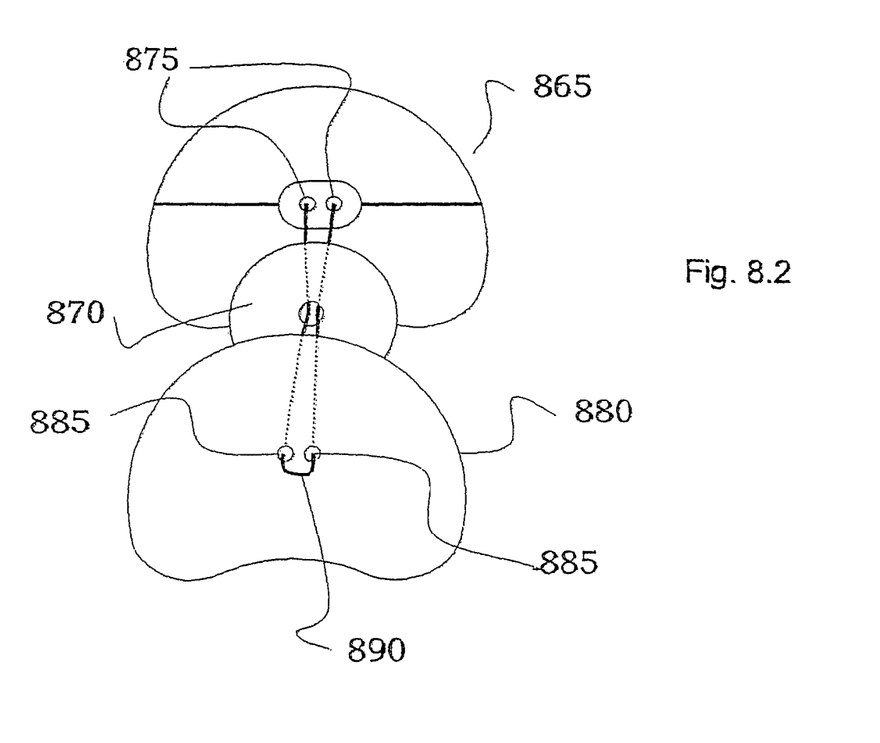

FIG. 8.1 illustrates an alternative means of connecting the two plates and supporting element together. In this example, the upper plate 810 and the lower plate 830 and the supporting element 820 are connected together with a plurality of threads introduced much like the attachment of a garment button on a jacket and so forth. This is illustrated more clearly in FIG. 8.2 in which the end plates 865 and 880 each have a pair of holes through them 875 and 885 through which multiple threads may be introduced. In this example, only one thread is shown 890 for reasons of clarity. The thread passes through a hole in the supporting element 870 so as to fix the element in position, but still allowing some relative movement between the plates and the supporting element. The thread may be permanent or of the resorbing type, made from one of several bioresorbable polymers known in the field. It is to be understood that the thread may be substituted by any suitable means of attachment, such as a plastic cable tie (tie-wrap) with ratchet mechanism as a means of allowing the tie to be fastened and adjusted to take-up the slack between the components.

Figure 9:
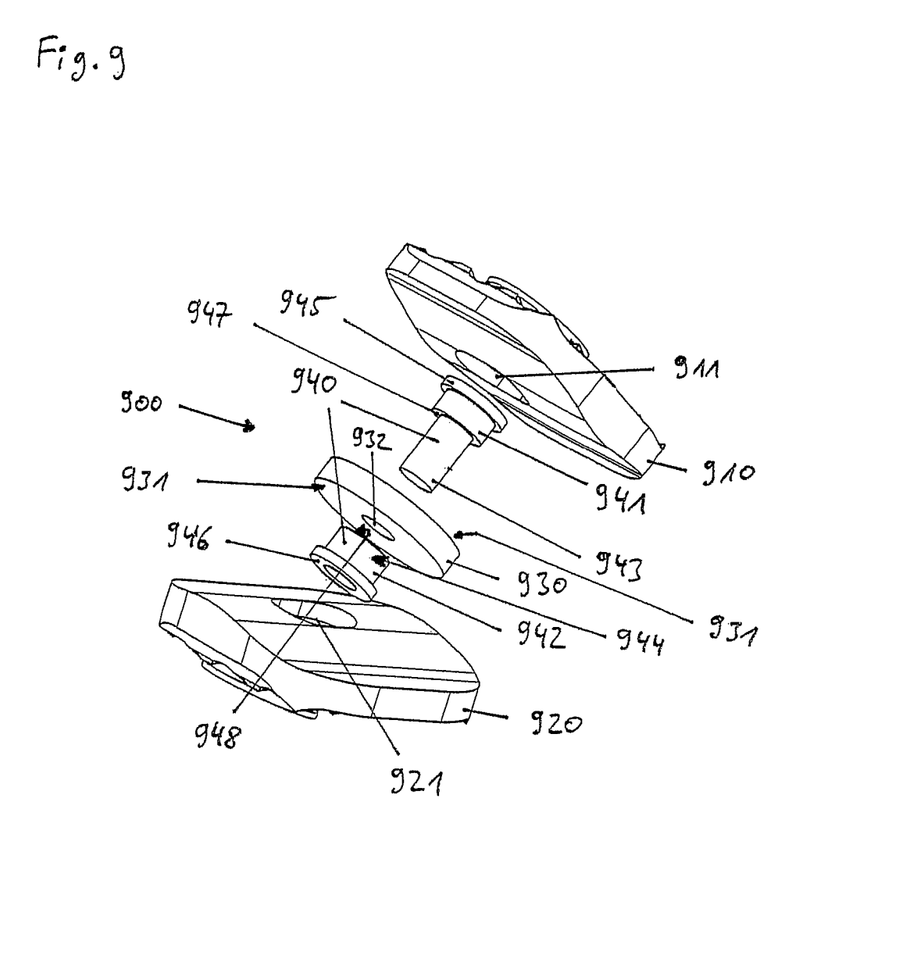
FIG. 9 is an exploded view of a device according to the present invention.

FIG. 9 shows a device 900 according to the present invention in an exploded view, comprising first and second plates 910, 920 and contacting element 930 which are assembled and fastened with each other by a mechanical fastening means 940. The mechanical fastening means is designed as a two-part bolt comprising first and second bolt parts 941, 942. The bolt provides raised locatable parts of the contacting elements which are locatable in the slots 911, 921 of the plates 910, 920. The plates 910, 920 are provided with through-holes which at the inner surfaces of the plates port into the slots 911, 921 and which port at the outer surfaces 912, 922 of the plates. The bolt parts 941, 942 can be introduced into the ports arranged at the outer surfaces of the plates so that the fastening portions 943, 944 of the bolt parts can be fastened with each other to assemble the device. The head portions 945, 946 of the bolt parts 941, 942 are located within the recesses of the plates and are arranged behind undercuts so that the plates cannot be separated from the bolt parts when they are fastened with each other. Especially, the fastening portion of bolt part 941 is designed as a pin which can be introduced into the sleeve-like fastening portion 944 of bolt part 942 to be fastened therein by form-fit means, especially by snap means and/or by friction means. The fastening portion or pin 943 of the bolt or of one bolt part passes through-hole 932 of contacting element 930, which preferably is arranged centrally at the contacting element. In its assembled state the rim portions 947, 948 of bolt parts 941, 942 engage the outer surfaces 931 of the contacting elements, which are engaged by the ridgelines of plates 910, 920. The shape of the fastening means, especially of the bolt, is designed in that the bolt can be shifted in the longitudinal direction of slots 911, 922 but can be shifted only slightly or neglectable in a direction perpendicular to the longitudinal direction of the slots.

Figures 10A, 10B, 10C, 10D, 10E, 10F:
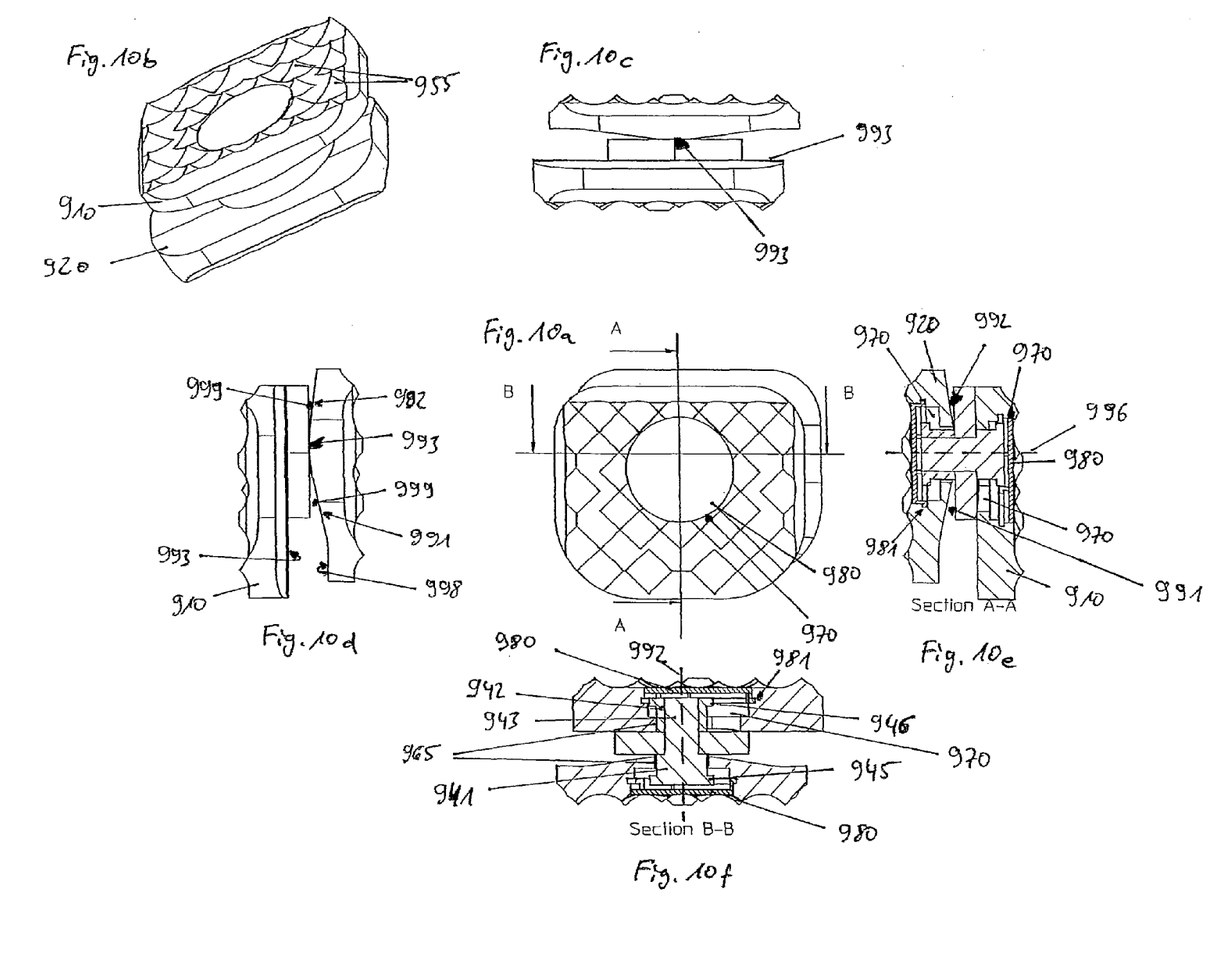
FIG. 10 shows different views of a device according to FIG. 9, wherein the first and second plates are arranged parallel to each other and are shifted against each other.

FIG. 10 shows an assembled device according to FIG. 9, wherein the plates 910, 920 are arranged parallel to each other. Obviously, the plates are shifted out of the centre of slot 911 and out of the centre of slot 922. As seen in the sectional views of FIG. 10e, 10f, the head portions 945, 946 of the bolt parts are arranged behind undercuts, which are provided by the portions 965 of the plates defining the slots 911, 922. The recesses 970 of both plates 910, 920 each are closed by a closure member 980 to avoid bone material to growth into recesses 970. The closure means are fastened at the plates by snap-in means, whereby the peripheries of the closure members may be provided with snap-in elements 981. To enable a tilting motion of the plates to each other, the head portions of the bolt can be shifted in the longitudinal direction of the bolt against the plates. Furthermore, which might be the case in any embodiment of the device according to the present invention, the sloping smooth surfaces 991, 992 of at least or of only one of the planes of plate 910 are designed differently. Especially, the sloping smooth surfaces may be designed as flat plates having different sloping angles or inclinations with respect to the main axis 996 being perpendicularly to the plates 910, 920. The surfaces having different design are arranged at opposite sides of the ridgeline 993 of the given plate. Similarly, the sloping smooth surfaces 991, 992 may have a different curvature in the sectional plane as shown in Figure 10b, i.e. a plane being perpendicular to the ridgeline of this plate, and/or in a plane perpendicular to this plane (not shown). In general, the sloping smooth surfaces of the other plate may be designed identically to each other so that this plate may be symmetrically (mirror plane) with respect to the ridgeline (see FIG. 10a).

Furthermore, as shown in FIG. 10, the sloping smooth surfaces may end at a distance apart from the circumference of the plate so that there may be a peripheral area 998 at the inner surfaces of the plates which may not be part of the sloping smooth surfaces. This peripheral area may be arranged at one or more sides of the plates, especially on adjacent sides in e.g. U-like shape or as a circumferential area.

Figure 11:
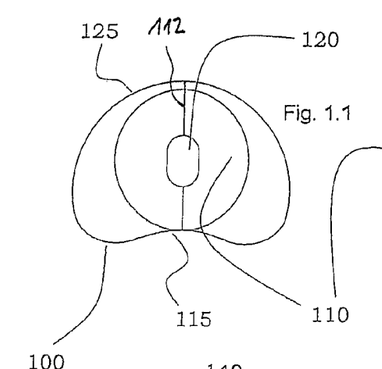
Figure 11A:
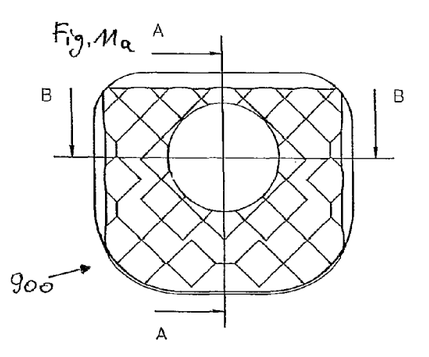
Figure 11B:
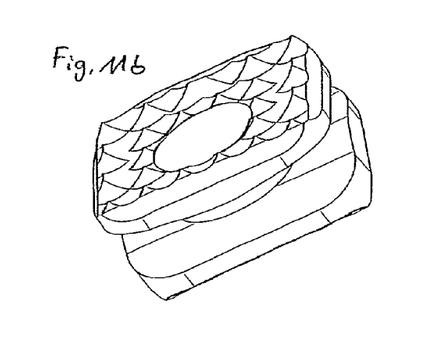
Figure 11C:
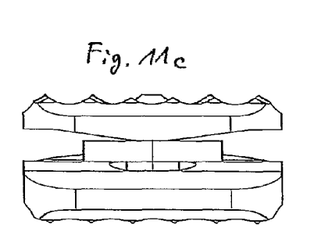
Figure 11D:
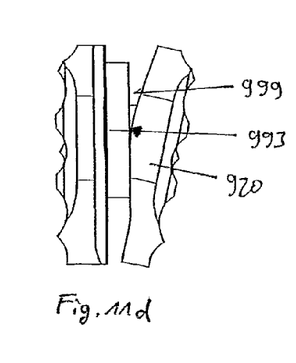
Figure 11E:
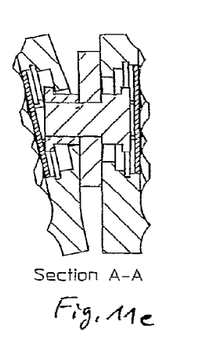
Figure 11F:
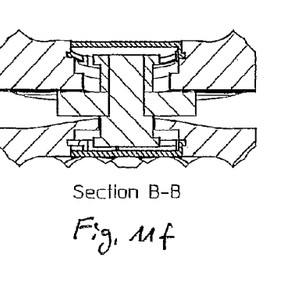
Figure 12:
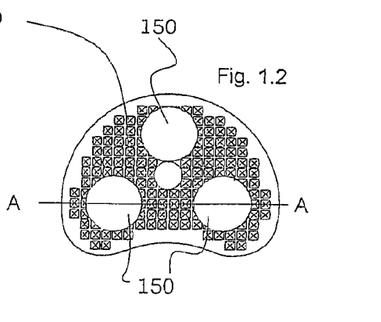
Figure 13:
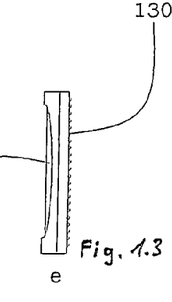
Figure 14:
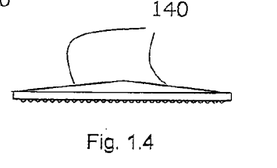
Figure 15:
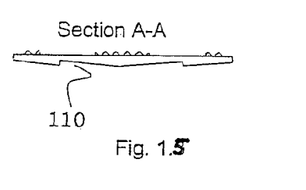
Figure 16:
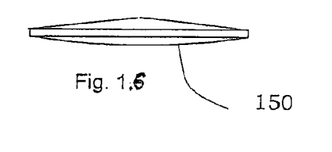
Figures 21, 25:
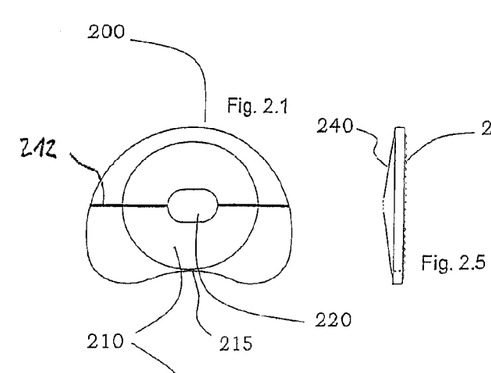
Figures 22, 23:
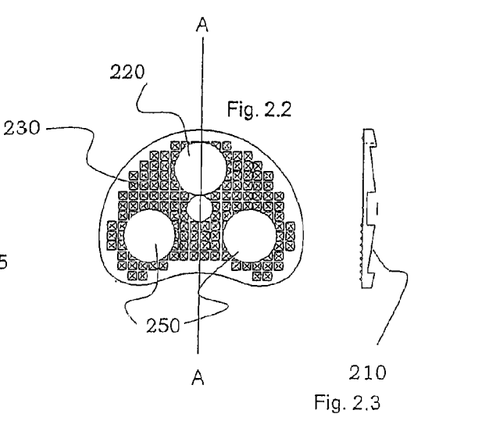
Figure 24:
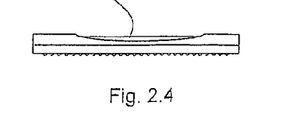
Figure 31:
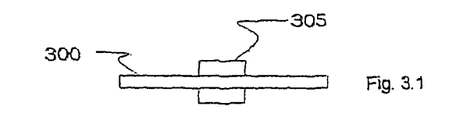
Figure 32:
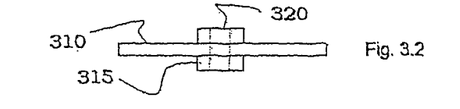
Figure 33:
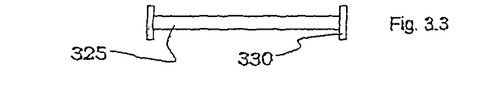
Figure 34:
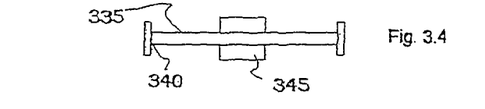
Figure 35:
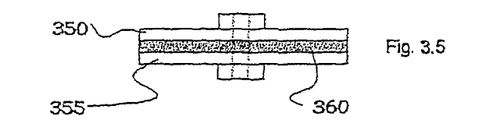
Figure 36:
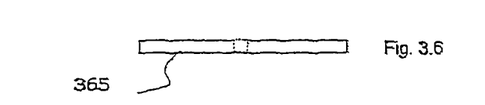
Figure 37:
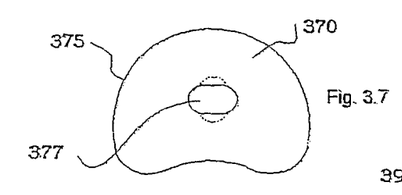
Figure 38:
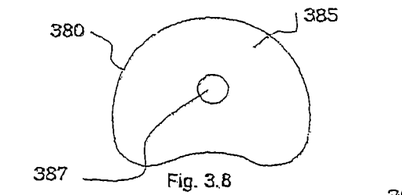
Figure 39:
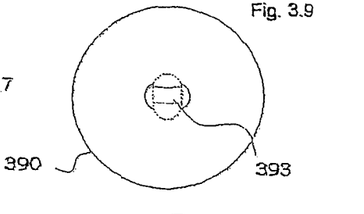
Figure 41:
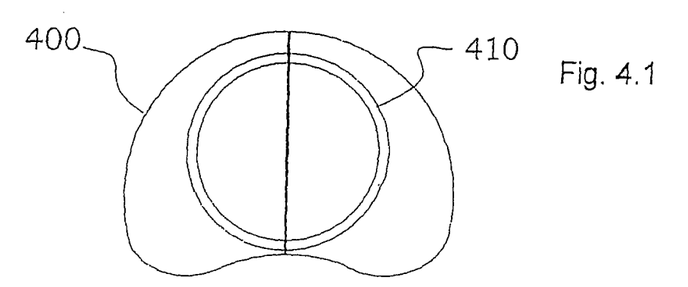
Figure 42:
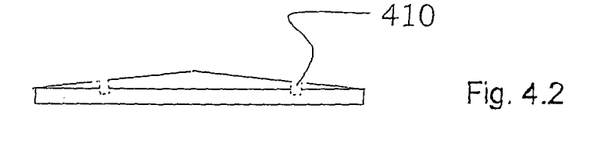
Figure 43:
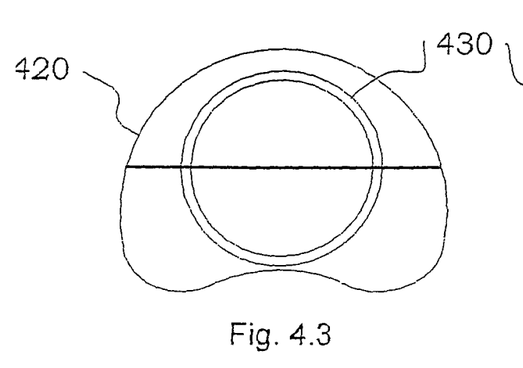
Figure 44:
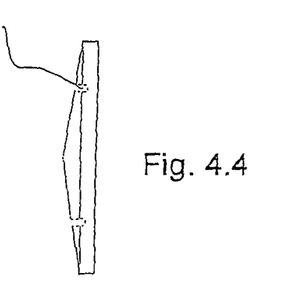
Figure 51:
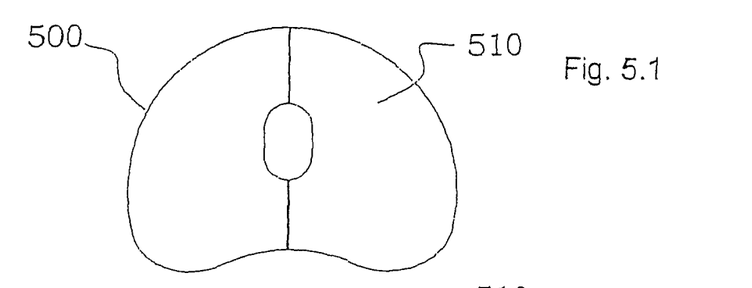
Figure 52:
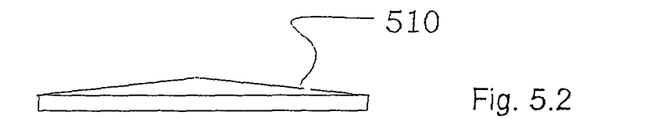
Figure 53:
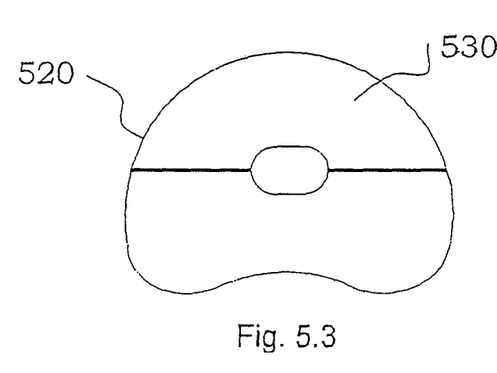
Figure 54:
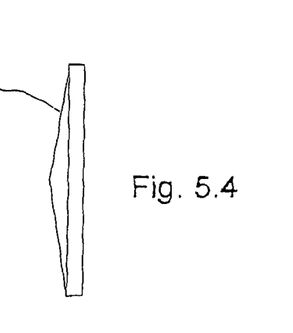
Figure 61:
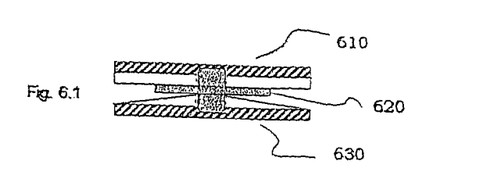
Figure 62:
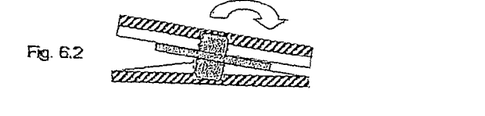
Figure 63:
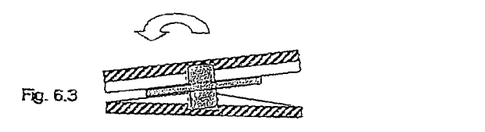
Figure 64:
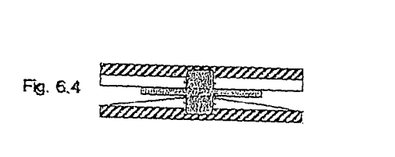
Figure 65:
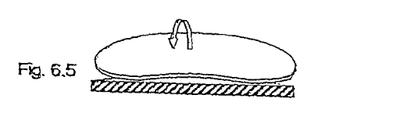
Figure 66:
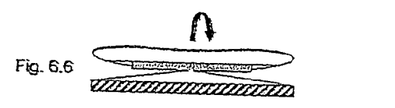
Figure 67:
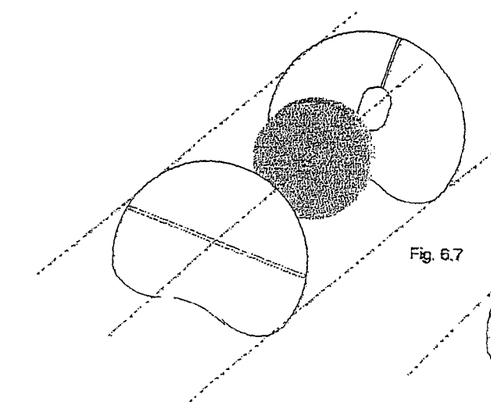
Figure 68:
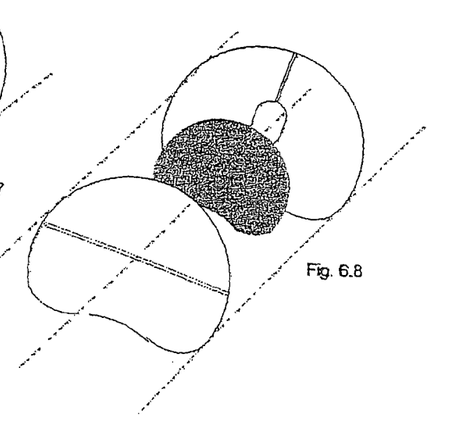
Figure 71:
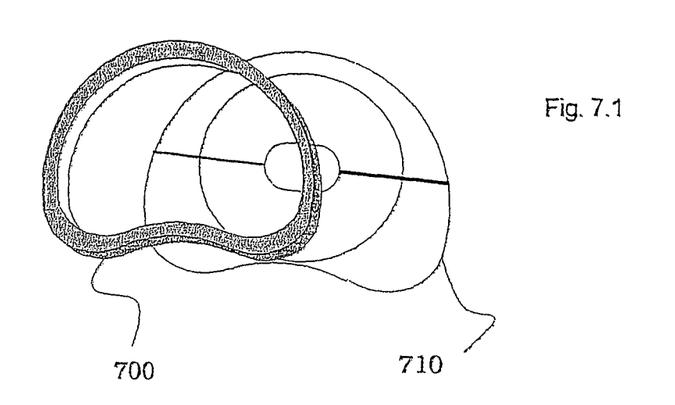
Figure 73:
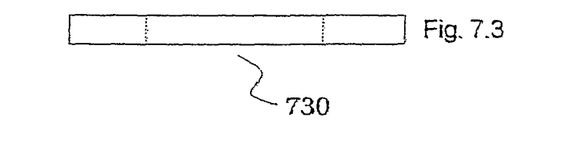
Figure 74:
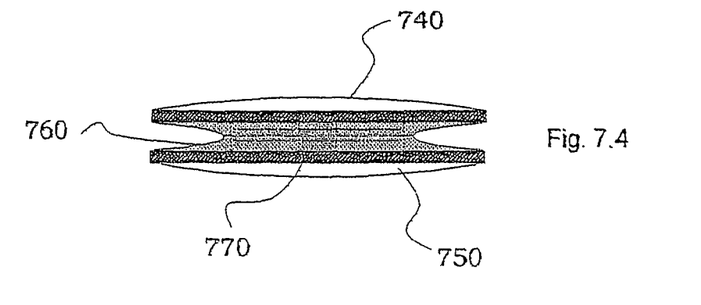

In general, the ridgelines may define the only portions of the plates being in permanent contact with the contacting element during a tilting or rolling motion of the plates relative to each other or relative to the contacting element. Accordingly, the outer surfaces of the plates in fact may be convex. In general, the outer surfaces of the contacting element facing the plates may be planar or may be curved in concave or convex manner as long as a tilting or rolling motion of the plates along the ridgelines is enabled. Accordingly, in any orientation of the plates to the contacting element, whether tilted against each other or not, may be a space 999 between the inner surfaces of the plates and the contacting element at height of the engaging area of the contacting element with the plates. The teeth 955 at the outer surfaces of both plates are arranged irregular. FIG. 11 shows different views of the device according to FIG. 9, wherein the first and second plates are tilted against each other. Especially, asymmetrical plate 920 is tilted around its ridgeline. In case the ridgeline is rounded, in general it might be very slightly spaced apart from the contacting surface of the contacting element in the tilted position of the plate. For seek of clearness, reference numerals are not shown.

Plates may be made from any suitable biomaterial, metals (for example, titanium alloys, cobalt chrome alloys, stainless steel alloys), biocompatible plastics, carbon fibre reinforced biocompatible plastics or ceramics (for example alumina or zirconia). The inner supporting element (stress distributor and spacer) may be made from the same selection of materials above, with a combination chosen for minimum wear and structural stability.

It will be appreciated that the present device is for placement between two adjacent vertebras as a spacer and stabiliser, without promoting bony fusion between the two vertebral bodies and which produces a reduced wear, whilst retaining normal spine motion in flexion, extension and lateral flexion, while providing stability in the anterior, posterior and lateral directions.

It will be further appreciated that the device can be placed into the intervertebral space in a way that does not promote an abnormal distribution of biomechanical stress on the patient's spine, whilst providing an artificial intervertebral disc with a plate attachment configured to attach to the adjacent bony surfaces above and below the artificial disc during implantation surgery and thereafter.

It is an artificial disc that is intended to conform to the concave bony surfaces of the adjacent vertebral body, which can be implanted anteriorly or translaminarly and provides an artificial disc that provides a centroid of motion centrally located within the vertebral space, whilst having low friction and wear.

The invention claimed is:

1. An intervertebral body spacer device for motion preservation, comprising first and second plates with inner and outer surfaces, said plates being disposed in a spaced apart relationship with the inner surface of the first plate facing the inner surface of the second plate, both inner surfaces being separated by a contacting element, wherein the contacting element comprises a disc including a central bore and wherein said inner surfaces of said first and second plates each form sloping surfaces that meet at a ridgeline, such that the ridgelines are disposed at an angle to one another, facing one another, and wherein the inner surface of at least one or both of the plates is non-planar, the plate having a middle and edges and being thicker towards the middle and thinner at the edges, the inner surface comprising at least two sloping smooth surfaces which meet at the ridgeline, the sloping surfaces are different in their sloping design, including different curvatures or different sloping angles.

2. An intervertebral body spacer device for motion preservation, comprising first and second plates with inner and outer surfaces, said plates being disposed in a spaced apart relationship with the inner surface of the first plate facing the inner surface of the second plate, both inner surfaces being separated by a contacting element having outer surfaces, wherein the contacting element is a substantially smooth flat element and wherein said inner surfaces of said first and second plates each form planar or non-planar sloping surfaces that meet at a linear ridgeline, such that the linear ridgelines are disposed at an angle to one another, facing one another, wherein the contacting element is made from a hard and stiff material and the outer surfaces of the contacting element facing the plates are planar, wherein contact between one or both of the plates and the contacting element is a line-to-line contact, and wherein at least one plate of the first and second plates is designed such that during a rolling motion of the plate, the ridgeline is separable from the contacting element, such that a portion of the inner surface of the plate being arranged just beside the ridgeline and out of contact with the contacting element will come in contact with the contacting element due to the rolling motion.

3. A device according to claim 2, wherein the inner surface of at least one or both of the plates is non-planar, the plate being thicker towards the middle and thinner at the edges, wherein further the inner surface comprises at least two sloping smooth surfaces that are substantially flat planes which meet at a ridgeline or the inner surface comprises at least two sloping smooth surfaces that are curved and that meet at a ridgeline or the inner surface of one plate comprises at least one sloping smooth surface that is curved and meets a ridgeline and that the inner surface of the other plate comprises at least one sloping smooth surface that is substantially flat plane which meets at a ridgeline.

4. A device according to claim 2, wherein the angle between facing ridgelines on opposing plate inner surfaces is substantially 90 degrees.

5. A device according to claim 2, wherein the inner surface of at least one or of both of the two plates has a locating slot.

6. A device according to claim 5, wherein the one or each locating slot is centrally disposed with respect to the plan form of the plate.

7. A device according to claim 5, wherein the long axis of the one or each slot runs along the ridgeline of the corresponding plate.

8. A device according to claim 2, wherein the contacting element is a smooth substantially flat element.

9. A device according to claim 8, wherein the contacting element has a raised locatable part extending above and below the upper and lower surface planes, said raised part locating into a receiving slot on the inner surfaces of the plates.

10. A device according to claim 9, wherein the raised part is a locatable cylindrical or elongated hub.

11. A device according to claim 10, wherein the hub has a substantially central bore through the thickness.

12. A device according to claim 2, wherein the contacting element is in the form of a disc.

13. A device according to claim 2, wherein the inner surface of at least one or both of the plates is non-planar, the plate being thicker towards the middle and thinner at the edges, the inner surface comprising at least two sloping smooth surfaces which meet at a ridgeline, the sloping surfaces are different in their sloping design, including different curvatures or different sloping angles.

14. A device according to claim 2, wherein the plates are connected together with the contacting element disposed between them.

15. A device according to claim 14, wherein the plates are connected together by mechanical means.

16. A device according to claim 15, wherein the mechanical means is a bolt being arranged in a through-hole of the contacting element and being fastened with opposite head portions at the first and second plates, respectively.

17. A device according to claim 16, wherein the bolt is a two-part member, each part being provided with a head portion which is arranged behind an undercut of a receiving area of the corresponding plate.

18. A device according to claim 16, wherein the bolt is a two-part member, the two parts are fastened with each other by form-fit means and/or by friction means.

19. A device according to claim 14, wherein fastening means for fastening the contacting element to the plates are provided, the fastening means having end portions which are arranged within a recess of the corresponding plate, the recess having a port being open towards the contacting element and having a port facing away from the contacting element, the later being closed by a closure means.

20. An intervertebral body spacer device for motion preservation, comprising first and second plates with inner and outer surfaces, said plates being disposed in a spaced apart relationship with the inner surface of the first plate facing the inner surface of the second plate, both inner surfaces being separated by a contacting element, wherein the contacting element is a disc, wherein said inner surfaces of said first and second plates each form planar or non-planar sloping surfaces that meet at a linear ridgeline, such that the linear ridgelines are disposed at an angle to one another facing one another, and wherein the inner surfaces of at least one or of both of the two plates has a locating slot wherein the long axis of the one or each slot runs along the ridgeline of the corresponding plate and wherein the contacting element has a raised locatable part extending above and below upper and lower surface planes of the contacting element, said raised part locating into the receiving slot on the inner surfaces of the plates, wherein the raised part of the contacting element is arranged in the slot with play in a longitudinal direction of the slot so that the raised part can be shifted predominantly in the longitudinal direction of the slot, and wherein at least one plate is rotatable around its main axis in relation to the contacting element.

21. An intervertebral body spacer device for motion preservation, comprising first and second plates with inner and outer surfaces, said plates being disposed in a spaced apart relationship with the inner surface of the first plate facing the inner surface of the second plate, both inner surfaces being separated by a contacting element having outer surfaces, wherein the contacting element is a disc and wherein said inner surfaces of said first and second plates each form planar or non-planar sloping surfaces that meet at a linear ridgeline, such that the linear ridgelines are disposed at an angle to one another, facing one another, wherein the contacting element is made from a hard and stiff material and wherein the outer surfaces of the contacting element facing the plates are planar or curved, and wherein at least one plate of the first and second plates is designed such that during a rolling motion of the plate, the ridgeline is separable from the contacting element, such that a portion of the inner surface of the plate being arranged just beside the ridgeline and out of contact with the contact element will come in contact with the contacting element due to the rolling motion so that in any orientation of the plates to the contacting element, whether tilted against each other or not, a space is located between the inner surfaces of the plates and the contacting element at a height of the engaging area of the contacting element with the plates, and wherein the inner surfaces of at least one or of both of the two plates has a locating slot wherein a long axis of the one or each slot runs along the ridgeline of the corresponding plate and wherein the contacting element has a raised locatable part extending above and below upper and lower surface planes of the contacting element, said raised part locating into the receiving slot on the inner surfaces of the plates and wherein both plates are rotatable around their main axis in relation to the contacting element.

* * * * *